United States Patent
Ginn

[19]

[11] Patent Number: 6,059,802
[45] Date of Patent: May 9, 2000

[54] DISSECTING RETRACTOR FOR HARVESTING VESSELS

[75] Inventor: Richard S. Ginn, San Jose, Calif.

[73] Assignee: Cardiothoracic Systems, Inc., Cupertino, Calif.

[21] Appl. No.: 09/032,744

[22] Filed: Feb. 27, 1998

[51] Int. Cl.$^7$ .................................................. A61B 17/22
[52] U.S. Cl. ...................... 606/159; 606/169; 606/167; 606/114; 606/181; 606/191; 606/194; 606/195; 606/198
[58] Field of Search ..................... 606/169, 167, 606/159, 191, 194, 195, 198, 181, 114, 222

[56] References Cited

U.S. PATENT DOCUMENTS

| | | | |
|---|---|---|---|
| 5,695,515 | 12/1997 | Orejola | 606/191 |
| 5,755,772 | 5/1998 | Evans et al. | 606/191 |
| 5,797,935 | 8/1998 | Barath | 606/159 |
| 5,817,127 | 10/1998 | Borodulin et al. | 606/167 |

*Primary Examiner*—Michael Buiz
*Assistant Examiner*—(Jackie)Tan-Uyen T. Ho
*Attorney, Agent, or Firm*—Lyon & Lyon LLP

[57] ABSTRACT

A surgical dissecting retractor for harvesting vascular conduits or vessels such as saphenous veins and the like is disclosed which dissects tissue and top and/or side branches from the vessel as it is advanced along a desired segment of the vessel via an entry incision in a patient's skin. The dissecting retractor is inserted while in a closed or "low profile" position to minimize trauma to the vessel and patient. Once installed above the vessel, the retractor is opened and locked to present a relatively "high profile", thereby creating and maintaining an enlarged working space or tunnel in the region between the skin and the vessel being harvested. Completion of the vessel harvesting procedure proceeds with suitable surgical instruments for dissecting, ligating, cauterizing and/or clipping, with or without visualizing devices which comprise further adjunct features of the retractors in accordance with the invention. Upon completion of the harvesting procedure, the dissecting retractor is unlocked to allow it to collapse to the closed position for removal from the harvesting site. A single surgeon can perform the harvesting procedure utilizing fewer instruments and with minimal trauma or damage to the vessel.

12 Claims, 4 Drawing Sheets

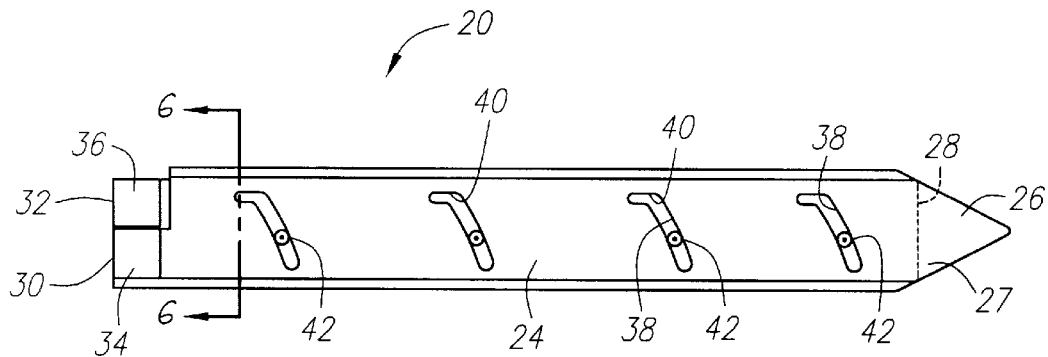
FIG. 3
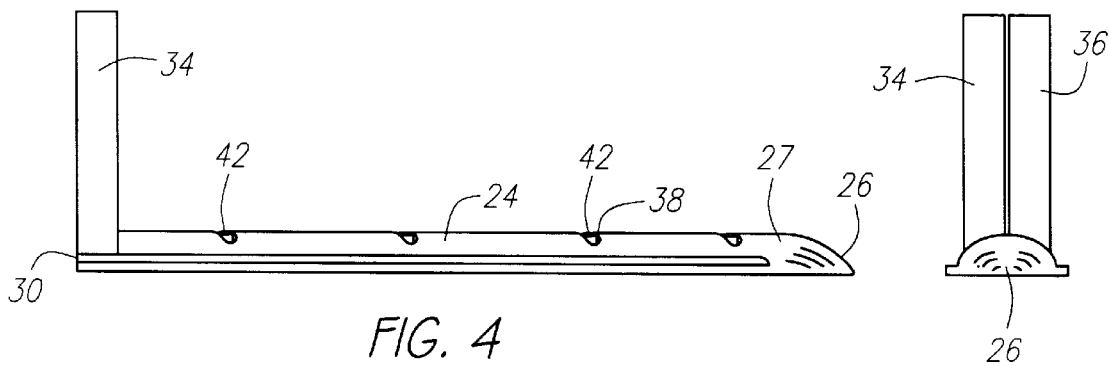
FIG. 4
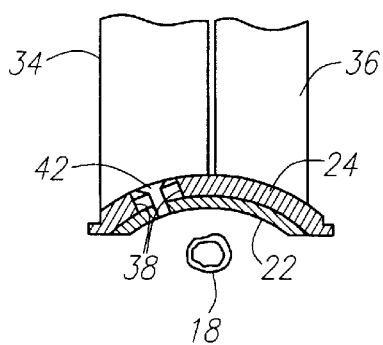
FIG. 5
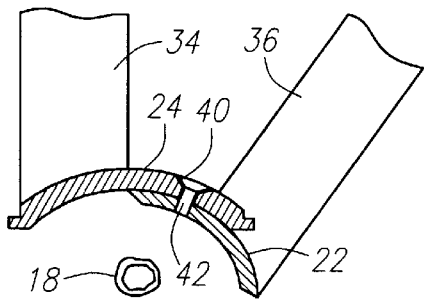
FIG. 6
FIG. 7
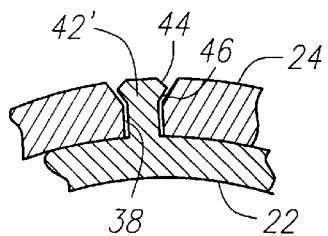
FIG. 8

DISSECTING RETRACTOR FOR HARVESTING VESSELS

FIELD OF THE INVENTION

The present invention relates to methods and instruments for harvesting vascular conduits or vessel sections, such as the saphenous veins, radial arteries and the like from a patient. More particularly, the present invention relates to methods and instruments for creating and maintaining a working space or tunnel over a vascular conduit or vessel in which other surgical instruments can be manipulated to complete the harvest of the vascular conduit or vessel section while minimizing trauma to the vascular conduit or vessel section and the patient.

BACKGROUND OF THE INVENTION

For various surgical procedures, and most commonly for coronary artery bypass grafting (CABG), it is common to remove or "harvest" a vascular conduit or vessel section, such as an artery or vein, from its natural location in a patient's body and to use it elsewhere in the body. In CABG surgery, the vascular conduit is used to establish a bypass between an arterial blood source and the coronary artery being bypassed. Often an artery proximate the heart, such as one of the internal mammary arteries, can be used as the bypass conduit. Alternatively, one or more of the saphenous veins in the legs, or a radial artery in an arm, are used as the vascular conduit, and are sometimes preferred by some surgeons in emergency situations, and where multiple bypass vessels are needed. For patient's requiring multiple bypasses, a surgeon may use the saphenous vein in addition to various arteries to revascularize a patient's heart.

The conventional surgical procedure used to harvest the saphenous vein and the like for use in the CABG surgery, is generally very traumatic to a patient. The procedure involves making a continuous incision in the leg for the full length of the desired vein section in order to provide adequate exposure for visualizing the vein and for introducing surgical instruments to sever, cauterize and ligate the tissue and side branches of the vein. The incision must then be closed by suturing or stapling along its length. Many patients suffer significant complications such as skin loss, infections and impaired healing, saphenous nerve damage, hematomas and may experience lower extremity discomfort for months. The procedure also leaves disfiguring scars, increases patient recovery time and hospital stay and thus adds to the cost of the CABG procedure.

In an attempt to overcome these problems, less-invasive techniques for harvesting vessels have been developed, employing one or two small incisions, generally one at each end of the section of vessel to be removed. Blunt mechanical force is applied by introduction of several surgical instruments of successively larger diameters to first create a working space in the tissue surrounding the vein while separating the vein from the surrounding tissue. Then further multiple instruments are introduced into the generally limited working space to dissect, clip and/or cauterize side branches of the vessel to allow harvesting of the desired section of the vessel. An endoscope generally is required for such a procedure to enhance visualization of the vessel and the surrounding tissue in the rather limited working space, particularly at a distance from the incision.

Even where these less invasive techniques reduce the overall length of the incision, the trauma to the vessel, the surrounding tissue and to the patient can be severe. In particular, the harvesting procedure itself may actually be lengthened and the trauma to the vessel potentially increased due to the number of surgical instruments that are needed for the harvesting procedure, and due to the fact that the instruments are reintroduced through the incision into the limited region between the patient's skin and vein. The trauma to the vessel as well as to the patient is exacerbated by the condition that the patient's skin and associated fat globules and tissue tend to collapse about the saphenous vein. It follows that in each withdrawal and subsequent insertion of a surgical instrument into the region above the vessel may cause added irritation, damage and trauma to the vessel. A nick in the vessel or damage to a side branch of the vessel causes undesirable problems since any damage to the harvested section of vessel must be repaired before it can be used as a graft. The repairs themselves are undesirable since they can lead to subsequent failure of the graft at the point of the damage and repair.

SUMMARY OF THE INVENTION

The goal of the present invention is to reduce the trauma and damage to the vessel being harvested as well as to the patient by providing the capability to more rapidly and less traumatically harvest the vessel. To this end, the invention is used to facilitate the creation of a working space around or above the vessel to be harvested. The working space created by the installation of the invention can then be enlarged if so desired. The enlarged working space can then be fixed and maintained by the invention itself, thereby minimizing the trauma caused by subsequent multiple insertions and withdrawals of additional surgical instruments. In addition, the invention enables a single surgeon to conduct the harvesting procedure.

Generally, the present invention includes an elongated slat assembly having a longitudinal axis and a width dimension transverse to the longitudinal axis, and means associated with the elongated slat assembly for varying the width dimension of the slat assembly. The elongated slat assembly provides a distal dissecting edge which preferably has a pointed tip for facilitating dissection of tissue away from the vessel to be harvested.

The slat assembly preferably includes at least two slats which are laterally translatable relative to each other. In one embodiment, there is an upper and a lower slat having similar cross-sections across their width dimensions. Preferably, the cross-section across the width of the slat assembly, and thus the individual slats, is arcuate. The means for varying the width dimension comprises means for laterally translating the slats relative to each other. Such means for laterally translating includes, for example, a handle at the proximal end of each slat.

To further enable the lateral translation of the assembly, a series of slots are formed in one of the slats and a corresponding series of pins are secured to the other slat with each pin being slidably contained by a corresponding slot. The slots may be formed at a selected angle relative to the longitudinal axis of the slat assembly or, alternately, slots are formed substantially transverse to the longitudinal axis. In the former design, the selected angle is preferably within the range from about 35° to about 90°. In a preferred design, the dissecting retractor includes means for maintaining an enlarged width dimension such that the width is greater than the minimum dimension and such that the width dimension can be fixed while a surgical procedure is conducted. Thus, when expanded, the retractor provides a stable, fixed, and maintained working space during the procedure. In the slot and pin embodiment, each slot includes a lock notch to enable a small longitudinal movement of the pins into respective lock notches to maintain the width dimension of the working space.

Another aspect of the invention includes a stand adjustably secured to respective handles for selectively raising the position of the elongated slat assembly to enlarge the working space above the vessel section to be harvested. Each stand includes a stand slot formed along the length thereof, a foot formed at a base of the stand, and bolt means disposed through the stand slot and threadably secured to the respective handle. In this way, each stand is vertically adjustable relative to the respective handle to maintain the selective raising of the position of the elongated slat assembly when the bolt means is tightened.

A method of using the present invention involves providing an elongated dissecting retractor for dissecting tissue and top and/or side branches from a vessel, such as the saphenous vein, a radial artery, or the like, during insertion of the dissecting retractor via an entry incision. Once installed, the invention maintains a working space in the region between the skin and the vein to act as a guide while allowing less traumatic manipulation of further surgical instruments, such as a ligating instrument, during the harvesting procedure. To this end, the dissecting retractor presents a low profile during its insertion, and subsequent removal, along the vessel via the entry incision. Further, the retractor is adapted to be expanded after installation to present a high profile and thus an expanded working space or tunnel above a selected length of vessel corresponding to the vessel section to be harvested. It follows that the use of any additional surgical instrument to complete the harvesting procedure is accomplished with less trauma to the vessel section even in the event that multiple insertions of surgical instruments is required.

In contrast to many of the vessel harvesting procedures practiced in the past, the use of the dissecting retractor of this invention requires the use of only a single instrument, the slat assembly, to separate the subcutaneous tissue from the vessel along a length of the vessel. As will be appreciated from the accompanying description, the slat assembly is inserted only once along the vessel, such as the saphenous vein. When repositioned to reorient the individual slat assemblies, the amount of retraction necessary to complete the harvesting procedure is essentially complete.

Note also that the repositioning of the slats relative to one another has the effect of increasing the surface area of the slat assembly which effectively amounts to the sum of the areas of the individual slats that are exposed when the instrument is repositioned from the "closed to" a partially or completely "open" position. The retraction achieved by the slat assembly is mechanical and bidirectional in nature because it relies on the rigid slat assemblies to move the tissue from the exertion of force along the length of the respective slats. The direction of the retraction is also dictated by the positioning of the slats in an orientation that is substantially parallel to the vessel to be harvested as seen in FIG. 1. Thus, the present invention enables a bidirectional mechanical retraction operation, subsequent to the positioning of the instrument along a length of the vessel and which is substantially parallel to the vessel to be harvested.

More particularly, the dissecting retractor of the invention comprises an elongated slat assembly or structure which includes a pair of elongated slats or blades preferably formed of a rigid or semi-rigid plastic material such as a glass filled polymer, or any other biocompatible medical grade plastic as well as a stainless steel, etc. The elongated slats preferably have an arcuate cross-section with an upper arcuate slat concentrically disposed upon a lower arcuate slat to allow the slats to slide a selected distance circumferentially as well as axially relative to each other. The distal end of either slat, but preferably the upper slat, is formed to define a tip which may be fairly pointed or sharp or to define a blade-like edge to facilitate the separation of tissue and side branches from a saphenous vein and the like as the dissecting retractor is advanced under the skin through an entry incision.

In one embodiment, the upper slat includes a spaced series of transversely, or preferably diagonally, arranged slots across the width of the slat. The lower slat includes a correspondingly spaced series of pins selectively fixed thereto with the heads of the pins extending from the lower slat in register with respective slots in the upper slat. The heads of the pins thus slidably secure the upper slat to the lower slat when assembled together. A handle is formed at the proximal ends of each of the upper and lower slats. When the handles, and thus the retractor are in a "closed" condition, the lower slat is nestled under and within the upper slat. Thus, the dissecting retractor presents a relatively low profile cross-section which facilitates advancing the distal tip of the retractor under the skin to thereby dissect the tissue and side branches from the saphenous vein as the tip of the dissecting retractor is advanced. When the dissecting retractor is in place above the length of the saphenous vein to be harvested, the handles are spread apart to "open" the retractor. In the open position, the lower slat is circumferentially displaced from its nestled position beneath the upper slat, thereby expanding the cross section of the slats and specifically the width and depth of the tunnel, or working space, created under the opened slats immediately above the length of vein. The retractor remains locked in place during the harvesting procedure and guides unobstructed insertions and withdrawals of a surgical instrument such as a ligating instrument, since the surrounding skin and tissue is held away from the working space over the saphenous vein. It follows that the visualization of the vein is much improved with or without use of an endoscope. However, the dissecting retractor may be modified in accordance with the invention for use with endoscopic or fiberoptic lighting devices, if desired.

Therefore, several modifications and alternative embodiments are contemplated in accordance with the invention as further disclosed in the following description.

BRIEF DESCRIPTION OF THE DRAWINGS

FIGS. 3, 4 and 5 are top, side and end views respectively of the invention of FIGS. 1 and 2, in a "low profile" closed position.

FIG. 6 is a cross-sectional view taken along section line 6—6 of FIG. 3, with the retractor in the low profile closed position.

FIG. 7 is a cross-sectional view taken along section line 7—7 of FIG. 2, with the retractor in the high profile opened position.

FIG. 8 is a cross-sectional view of a fragment of a lower slat illustrating a pin configuration which is integrally preformed with the slat.

DETAILED DESCRIPTION OF THE PREFERRED EMBODIMENTS

Figure 1:
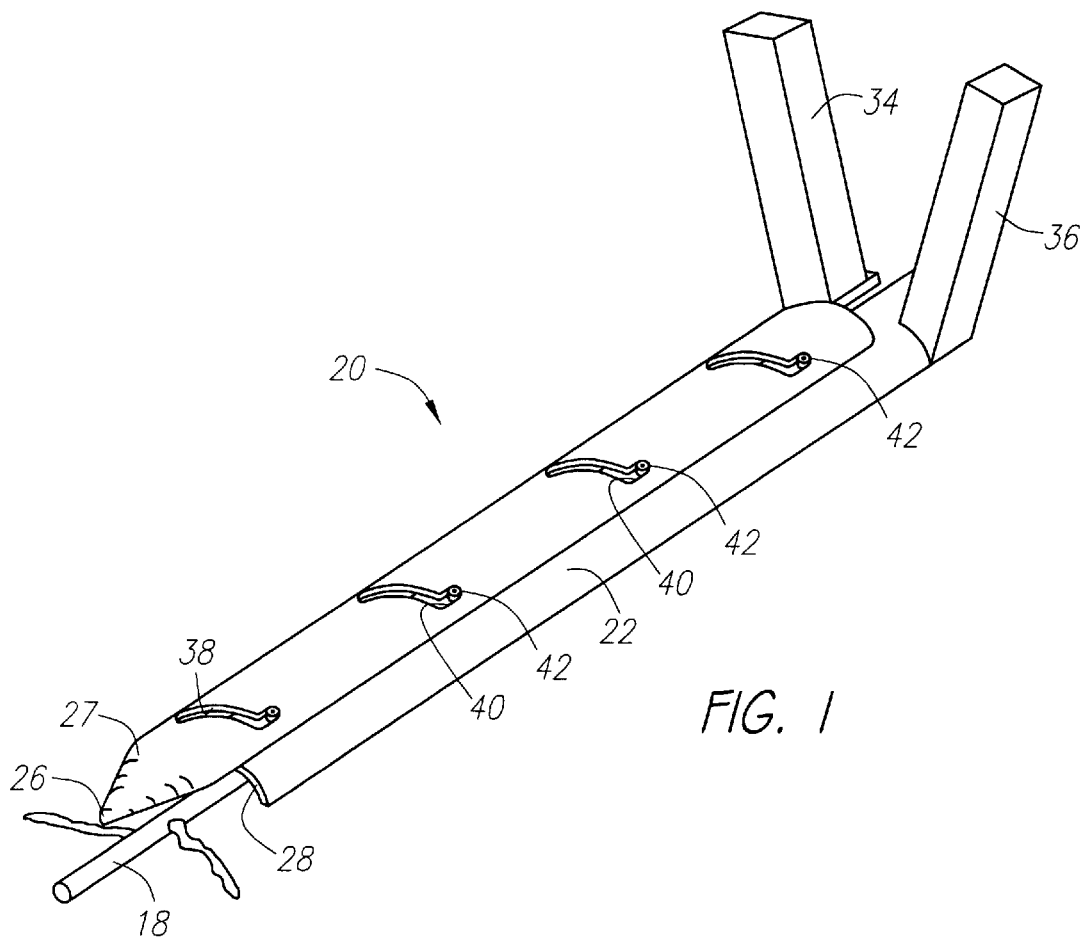
FIG. 1 is a perspective view illustrating an embodiment of a dissecting retractor of the invention in a "high profile" opened position.

FIG. 1 illustrates a preferred embodiment of the dissecting retractor 20 of the present invention, in a relatively "high profile" opened position over a vessel 18 such as a saphenous vein, a radial artery, etc. The invention comprises an elongated slat assembly or structure which includes a lower blade or slat 22 nestled beneath an upper blade or slat 24, wherein the slats are preferably arcuate in the direction of their widths and form an arcuate cross section. The arc of each slat has essentially the same radius, and the width and thickness of the lower slat 22 generally is less than the width and thickness of the upper slat 24, so that the lower slat 22 fits snugly within the arcuate circumference of the upper slat 24 when the retractor is in a "low profile" closed position. See for example FIG. 6. The distal end 27 of the upper slat 24 preferably extends beyond a distal end 28 of the lower slat 22. Preferably, distal end 27 of upper slat 24 defines a downward curving configuration and terminates at a pointed and sharpened tip 26.

To facilitate the process of installing the dissecting retractor 20, the retractor may be oriented into the low profile or closed position, as illustrated in FIGS. 3–6, which presents a minimal cross section and also presents tip 26 as the leading edge of the dissecting retractor to perform the function of dissecting tissue and top and/or side branches from a vessel 18 as the surgeon advances the dissecting retractor along the vessel via an entry incision (not shown).

Figure 2:
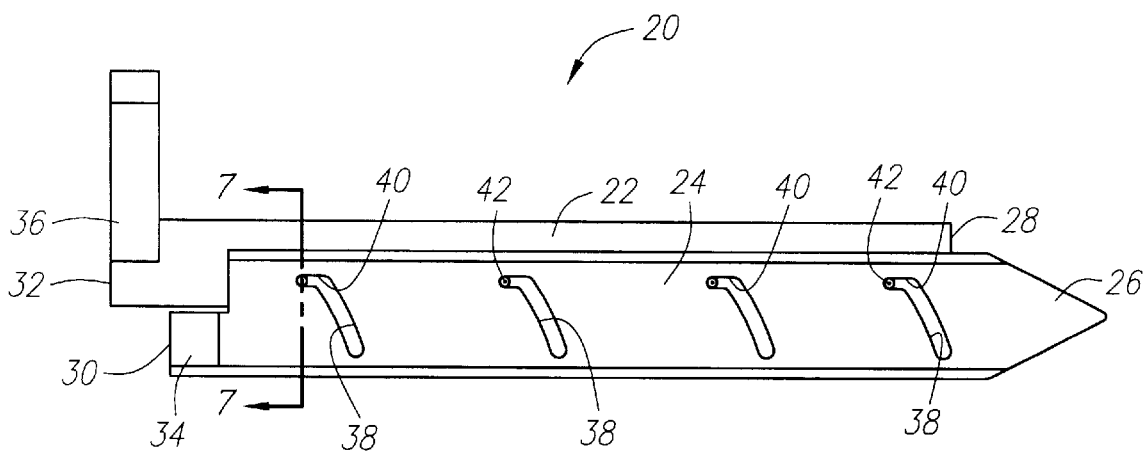
FIG. 2 is a top view of the embodiment of FIG. 1 in the opened position.

Referring to FIGS. 1 and 2, proximal ends 30, 32 of the upper and lower slats 24, 22, respectively, have respective handles 34, 36 integrally formed thereto, which handles extend generally perpendicular to the lengths of the respective slats. When the slats are in the closed position, the handles 34, 36 extend upward in side-by-side configuration so that they can be grasped by one hand for insertion of the dissecting retractor. The handles 34, 36 are configured, at the points of attachment to upper and lower slats 24, 22, to allow the handles to be positioned in close proximity when the dissecting retractor 20 is in the closed position. Thus, the width of either handle is less than the length of the arc defined by the upper or lower slats 24, 22 respectively. Preferably, a cut-out portion of the upper slat 24 is provided to allow conforming engagement of the handle 36 affixed to lower slat 22 with the handle 34 of upper slat 24 to allow the upwardly extending handles to be positioned as close to one another as possible. This configuration is best illustrated in the right side of FIG. 1. Essentially, a half portion of a short length of the proximal end 30 of the upper slat 24 is removed to provide space for the upwardly extending handle 36 of the lower slat 22 when the retractor is in the closed position.

When it is desired to move the slats 22, 24 to the open position, the handles 36, 34 are spread apart a selected distance as depicted in FIGS. 1, 2 and 7 and further described below.

To vary the width dimension of the slide assembly, the upper slat, 24 is provided with a series of spaced, identical slots 38 which, in this embodiment, extend diagonally at a selected angle across a major portion of the slat's width. See, for example FIGS. 1, 2 and 3. The slots 38 terminate at similar ends in a lock notch 40, whose relatively short length extends generally parallel with the length of the slat 24. The lock notches 40 are used to lock the retractor 20 in the high profile opened position, as further described below. A corresponding series of pins 42 having heads of a selected type and diameter and are molded, screwed into, or otherwise securely fastened to the lower slat 22. The pins 42 are preferably spaced apart the same distances as are the corresponding slots 38 so that each slot has an associated pin. Installation of the pins 42 through their respective slots 38 and into the slat 22, provides assembly of the upper slat 24 to the lower slat 22 while allowing translation therebetween in the direction of the diagonal slots 38 and of the lock notches 40. The heads on the pins 42 may be of round head or flat head configuration, and preferably are recessed or countersunk within the slots 38 and lock notch 40 so that they do not snag tissue when the retractor is being installed and used. See for example FIGS. 6, 7 and 8. The slot-and-pin-type assembly is merely one example of a mechanical configuration that varies the width of the slide assembly. Others include a lead screw or other mechanical expedient.

When it is desired to remove the dissecting retractor from the harvest site, such as upon completion of the harvesting procedure, in this embodiment, the pins 42 are unlocked from the lock notches 40 by pushing the lower slat 22 distally relative to the upper slat 24, and the handles 34, 36 are closed together to return the retractor to the closed low profile position. The retractor then is withdrawn from the harvesting site via the entry incision.

Pins 42 may be formed of a metal such as, for example, stainless steel, however it is to be understood that the pins 42 may be pre-formed of a plastic material similar to that of which the slats 22, 24 and handles 34, 36 are formed. That is, referring particularly to FIG. 8, lower slat 22 may be formed in a molding process including the handle 36, with pre-formed plastic pins 42' integrally formed with the slat 22. The heads of the pre-formed pins 42' include a partially beveled top surface 44 and a countersunk lower surface 46 to allow the pins 42' to be snapped into respective similarly beveled slots 38. See FIGS. 6, 7 and particularly FIG. 8. As may be seen, the heads of the pins 42 and/or 42' thus are countersunk to lie flush with the upper surface of the upper slat 24. Accordingly it is to be understood that various types of materials and various different configurations of slats, handles and/or pins may be employed to form the components of the dissecting retractor of the present invention.

Figure 9:
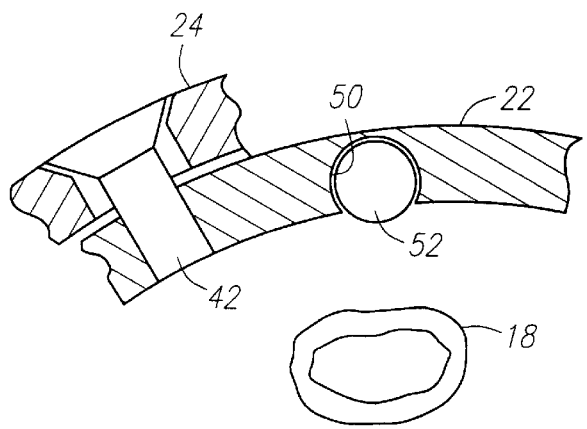
FIG. 9 is a cross-sectional view of a portion of the retractor illustrating a modified embodiment employing a slotted lumen in the lower slat, through which an endoscope or a fiberoptic light device may be slidably disposed to facilitate visualizing the length of the saphenous vein during the harvesting procedure.
Figure 10:
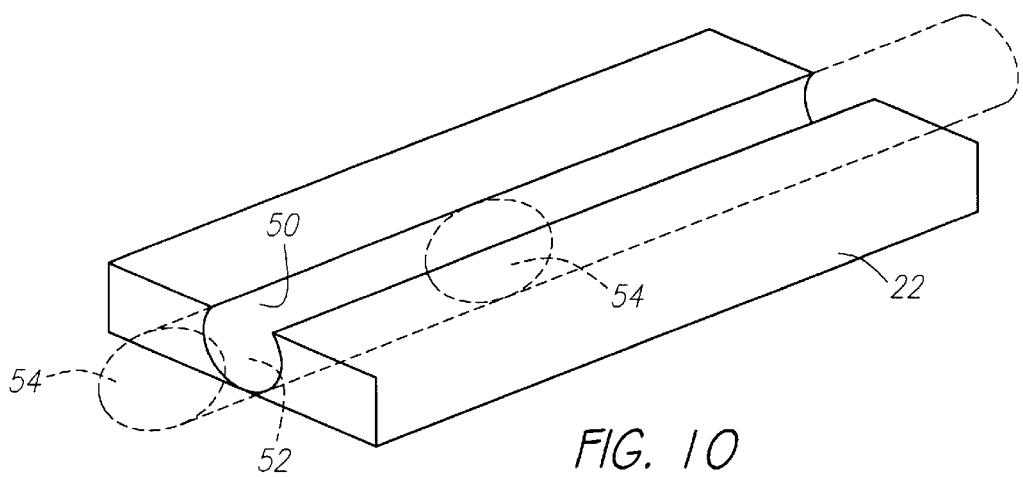
FIG. 10 is a partial bottom view of the embodiment of FIG. 9 further illustrating the slotted lumen within which the endoscope or light device is translatable.

FIGS. 9 and 10 illustrate a modified embodiment of the present invention wherein the lower slat 22 is modified to include a partially exposed lumen 50 which generally extends the length of lower slat 22. The lumen 50 is formed within the thickness of lower slat 22 and is exposed along an arcuate lower portion of its length to the minimal working space created beneath the lower slat 22 when the retractor is closed, and to the expanded working space formed under the lower and upper slats 22, 24 when the retractor is opened. An endoscope or a fiberoptic light device, herein indicated by numeral 52, may be inserted in the lumen 50 and may be translated along the lumen to any position along the retractor which is desired to visualize a corresponding location along the saphenous vein, radial artery or the like, depicted by numeral 18 in FIG. 9. FIG. 10 illustrates the use of an endoscope 52 which may be translated along the lumen 50 to selectively position a lens 54 of endoscope 52 in a desired position relative to the vessel. A fiberoptic light device may be similarly used and positioned.

Figure 11:
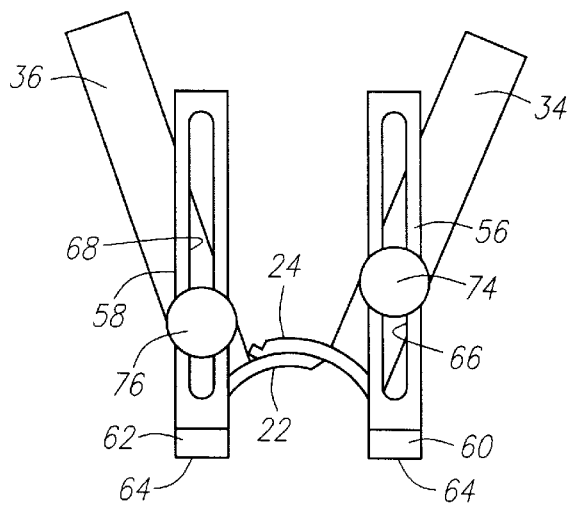
FIGS. 11 and 12 are end and side views respectively of another modified embodiment of the invention.
Figure 12:
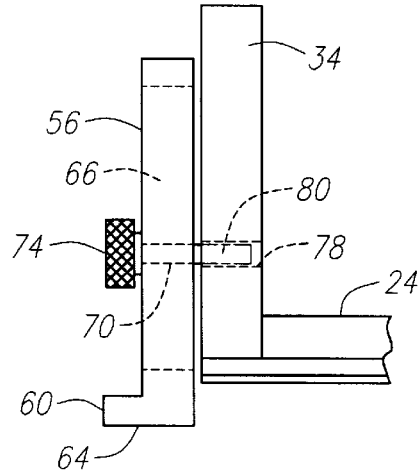

Referring to FIGS. 11 and 12, an alternative modification of the present invention provides means for further enlarging the working space created by the dissecting retractor after installation over a vessel via an entry incision. To this end, each of the handles 34, 36 is provided with an adjustable stand 56, 58, respectively, which terminate at the lower ends thereof in a respective foot 60, 62. The bottom of each foot is preferably provided with a high traction material or surface 64 to prevent any slippage of the retractor relative to the harvesting site. The stands 56, 58 are provided with respective stand slots 66, 68, and each include respective bolts 70 threaded at one end and provided with a knurled knob 74, 76 at the other end. A threaded bore (78 in FIG. 12) is provided in each handle 34, 36 to threadably receive the threaded ends (80 in FIG. 12) of respective bolts 70. As may be seen, once the dissecting retractor is installed in place, loosening the bolts 70 and lowering the stands 56, 58 relative to the handles 34, 36 tends to raise the proximal ends 30, 32 of the retractor. This in turn, further enlarges the working space available above the vessel being harvested. Tightening the knobs/bolts secures the stands 56, 58 and the raised dissecting retractor in place. It follows that a surgeon working alone can proceed with completion of the vein harvesting procedure with suitable surgical scissors, ligating instrument, cauterizing instrument and/or surgical clips as required, and with or without visualizing instruments such as the endoscope or fiberoptic light device 52 of previous mention. That is, use of the adjustable stands 56, 58 can allow a surgeon to perform the harvesting under direct visualization, without need for an endoscope or light device.

Figure 13:
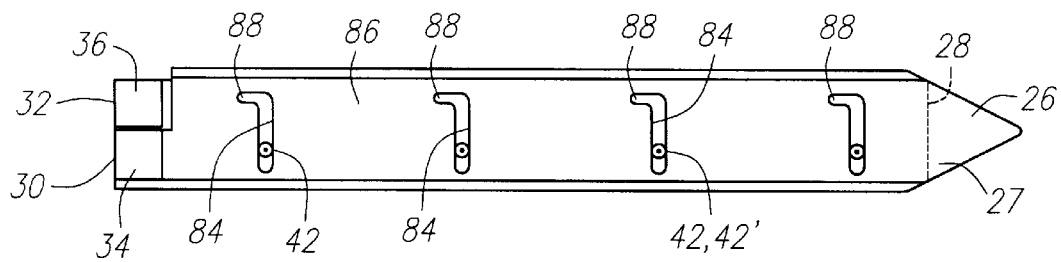
FIGS. 13 and 14 are top views of a further embodiment of the invention in closed and opened positions respectively.
Figure 14:
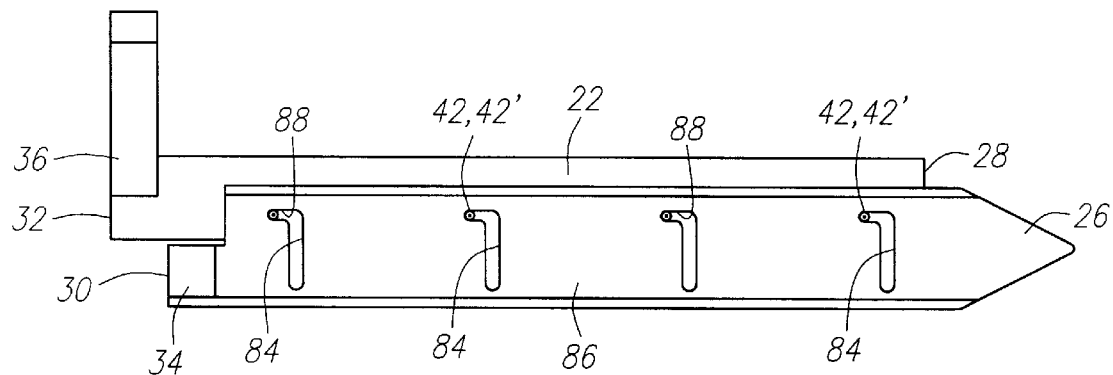

FIGS. 13 and 14 illustrate a further modification of the previous embodiments of the invention, namely, the re-orientation of the diagonal slots 38 of the previous figures to illustrate generally transverse slots 84 relative to the length of an upper slat 86, which otherwise is similar to the slat 24 of previous description. The slots 84 terminate at similar ends in respective lock notches 88 which extend a short distance in a generally longitudinal direction of the upper slat. FIG. 13 illustrates the dissecting retractor in a closed low profile position used when the retractor is advanced through an entry incision and provides dissection of tissue and top and/or side branches by means of the sharpened tip 26.

FIG. 14 illustrates the retractor after it has been installed in position and opened to present a high profile to create an enlarged working space over the vein or artery to be harvested. The lower slat 22 is locked in the open position relative to the upper slat 86 by shifting the lower slat proximally to engage the pins 42 (or 42') in the lock notches 88. This maintains an enlarged width dimension and prevents the retractor from collapsing and closing due to the forces applied by the surrounding tissue and skin, until desired by the surgeon.

Figure 15:
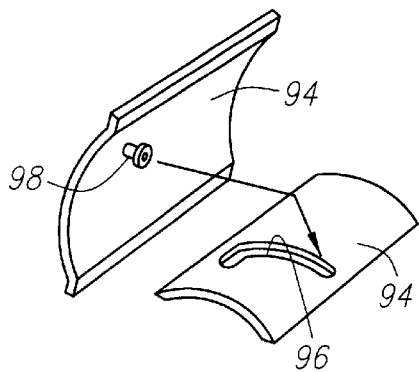
FIG. 15 is a fragmentary, exploded, perspective view of another embodiment of the invention wherein the pins are located on the upper slat and the slots are formed in the lower slat.

FIG. 15 illustrates an alternative embodiment of the invention wherein the positioning of the pins and associated slots are reversed. That is, a lower slat 92 corresponds to the lower slat 22 and an upper slat 94 corresponds to the upper slat 24, of previous description, except that a series of slots 96, similar to the previous slots 38 or 84, are formed in the lower slat 92. Likewise, a corresponding series of pins 98, similar to the previous pins 42 or 42', are secured to or formed with the upper slat 94. In this configuration, the upper surface of the upper slat 94 is smooth along its entire length with no obstructions to the tissue and branches during the procedures of installation and expanding of the dissecting retractor in accordance with the invention.

Accordingly, although the present invention has been described herein relative to specific embodiments and modifications, various additional features and advantages will be apparent from the description and drawings, and thus the scope of the invention is defined by the following claims and their equivalents.

What is claimed is:

1. A method of harvesting a section of vessel via an entry incision in a patient's skin, comprising the steps of:

introducing an elongated low profile structure along a length of the vessel to dissect tissue from the vessel; and expanding the width of the structure laterally to define a structure of relatively high profile which creates a corresponding enlarged working space under the skin above the length of the vessel for subsequent manipulation of further surgical instruments to complete the harvesting.

2. The method of claim 1 wherein:

said elongated low profile structure includes a first elongated slat nestled within a second elongated slat to present said low profile during said step of introducing; and said step of expanding includes laterally spreading apart said first and second elongated slats to expand the width of said structure and create the enlarged working space.

3. The method of claim 2 including the steps of:

locking said first and second slats apart to maintain said high profile structure and the enlarged working space during completion of the vessel harvesting.

4. The method of claim 3 including the step of:

further elevating said high profile structure to correspondingly increase the enlarged working space between said structure and the vessel being harvested.

5. The method of claim 4 including the steps of:

unlocking said first and second slats;

collapsing said first and second slats together laterally to re-establish said low profile structure; and removing said low profile structure from under the skin via the entry incision after harvesting the section of vessel.

6. A method of harvesting a vein and the like via an entry incision in a patient's skin, comprising the steps of:

introducing an elongated slat assembly, having a closed low profile cross section, into the entry incision and above the vein;

advancing the slat assembly along the vein for a desired length of the vein while dissecting tissue from the vein; and expanding the width of the slat assembly after it is advanced the desired length to create a relatively high profile and a corresponding enlarged working space above the length of the vein for subsequent atrallmatic manipulation of selected surgical instruments within the enlarged working space to complete the harvesting.

7. The method of claim 6 including the steps of:

locking the expanded slat assembly in the high profile position; and further elevating the expanded slat assembly to correspondingly further expand the enlarged working space in a region between the patient's skin and vein.

8. A method to mechanically retract the tissue along a length of a vessel comprising:

inserting an elongated slat assembly comprised of at least two rigid slats through subcutaneous tissue proximate to the vessel, wherein said slat assembly is in a closed position, and operating a means associated with said elongated slat assembly to increase the width of the slat assembly by repositioning the at least two rigid slats to an open position.

9. The method of claim 8 wherein the mechanical retraction is substantially parallel to the vessel.

10. The method of claim 9 further comprising the step of fixing the position of said slot assembly in an open position.

11. The method of claim 2 wherein said first elongated slat and said second elongated slat are substantially rigid.

12. The method of claim 2 wherein said first elongated slat and said second elongated slat have arcuate shaped cross-sections.

* * * * *